(12) United States Patent
Lyu (10) Patent No.: US 9,163,250 B2
(45) Date of Patent: Oct. 20, 2015

(54) TRUNCATED GLYCERALDEHYDE-3-PHOSPHATE DEHYDROGENASE PROMOTER

(71) Applicant: MYCOMAGIC BIOTECHNOLOGY CO., LTD., New Taipei (TW)

(72) Inventor: Ying-Tzu Lyu, New Taipei (TW)

(73) Assignee: MYCOMAGIC BIOTECHNOLOGY CO., LTD., Taipei County (TW)

( * ) Notice: Subject to any disclaimer, the term of this patent is extended or adjusted under 35 U.S.C. 154(b) by 249 days.

(21) Appl. No.: 13/662,031

(22) Filed: Oct. 26, 2012

(65) Prior Publication Data

US 2014/0123345 A1    May 1, 2014

(51) Int. Cl.
*C12N 15/80* (2006.01)
(52) U.S. Cl.
CPC ...................................... *C12N 15/80* (2013.01)
(58) Field of Classification Search
None
See application file for complete search history.

(56) References Cited

U.S. PATENT DOCUMENTS 7,777,021 B2 * 8/2010 Kuo ............................ 536/24.1

OTHER PUBLICATIONS

Kuo__Appl Microbiol Biotechnol__65__593__2004.*
Kuo__Bot Stud__51__303-09__2010.*
Bruns__Mol Ecol__7__257__1998.*
Chrispeels__Plant Cell__3__1-9__1991.*
Gardes__Mol Ecol__2__113__1993.*
Potenza__In Vitro Cell Dev Biol Plant__40__1__2004.*
Dornenburg__Enz Microbiol Tech 17__674__1995.*

* cited by examiner

*Primary Examiner* — Medina A Ibrahim
*Assistant Examiner* — Russell Boggs
(74) *Attorney, Agent, or Firm* — WPAT, P.C.; Anthony King; Kay Yang (57) ABSTRACT

The invention found that partial deletion of the glyceraldehyde-3-phosphate dehydrogenase (gpd) promoter can enhance gene expression (even heterologous gene expression) in basidiomycetous fungi. With the discovery of these gpd promoters, an expression system can be constructed for the expression of a heterologous gene in mushroom. Accordingly, the invention provides a truncated glyceraldehyde-3-phosphate dehydrogenase promoter and a construct comprising the promoter of the invention operably linked to a heterologous transcribable polynucleotide molecule and a mushroom comprising the construct.

12 Claims, 8 Drawing Sheets

TRUNCATED GLYCERALDEHYDE-3-PHOSPHATE DEHYDROGENASE PROMOTER

FIELD OF THE INVENTION

The invention relates to a truncated glyceraldehyde-3-phosphate dehydrogenase promoter and a construct comprising the promoter of the invention operably linked to a heterologous transcribable polynucleotide molecule.

BACKGROUND OF THE INVENTION

Molecular pharming has attracted extensive attention in production of various pharmaceutical proteins, including enzymes, vaccines, antibodies, hormones, etc. Edible mushrooms are regarded as appropriate hosts for production of recombinant proteins, especially for the development of edible vaccines. The use of mushrooms for molecular pharming has all the advantages of plant-based systems coupled with unique benefits including complete duplication, fast growth, scale-up production under controlled conditions and less gene contamination. However, the success of mushroom molecular pharming relies on efficient transformation and gene expression.

Using strong promoters to express heterologous genes in appropriate hosts is a major strategy in biotechnological applications. The glyceraldehyde-3-phosphate dehydrogenase (GPD, EC 1.2.1.12) promoter is a strong constitutive promoter which can be induced by any carbon source and has been widely used in the expression of heterologous proteins in *Saccharomyces cerevisiae, Pichia pastoris* and other yeasts. GPD is one of the key enzymes in the glycolytic and gluconeogenesis pathway and comprises up to 5% of the soluble cellular protein content in *S. cerevisiae* and other higher eukaryotes. Furthermore, gpd mRNA accounts for 2-5% of the poly $(A)^+$ RNA present in yeasts. These observations suggest that the gpd gene is regulated by a highly active promoter. In fact, vectors carrying the homologous gpd promoter region have been reported to be efficient in directing expression of heterologous genes in yeasts (Bitter and Egan, 1988, Doring et al., 1998, Eriksson et al., 1995, Vassileva et al., 2001) and filamentous fungi (Juge et al., 1998, Punt et al., 1987). However, known expression vectors containing genetic regulatory elements for expression in filamentous fungi of the ascomycetes class cannot be efficiently expressed in filamentous fungi of the basidiomycetes class.

The gpd genes have also been cloned from basidiomycetous fungi, including *Schizophyllum commune, Phanerochaete chrysosporium, Agaricus bisporus* (Harmsen et al., 1992), and *Lentinula edodes*. Among these mushrooms, genetic transformation using homologous gpd promoter was reported successful only in *A. bisporus, Flammulina velutipes* and *L. edodes* (Hirano et al., 2000, Kuo et al., 2004, van de Rhee et al., 1996). Although heterologous promoters have been used for the expression of drug-resistant marker genes, the genetic transformation is not sufficient to express heterologous genes. To sufficiently and effectively express a heterologous gene, it is important for a host cell to recognize the promoter sequence by its transcriptional machinery. Chun-Yi Kuo et al. demonstrated that a heterologous gene, hygromycin B phosphotransferase gene (hpt), can be expressed in *F. velutipes* (Kuo et al., 2004). However, it was found that the gpd genes in some basidiomycetous fungi, though highly similar, are significantly different in their promoter regions. U.S. Pat. No. 7,777,021 provides an isolated glyceraldehyde-3-phosphate dehydrogenase promoter in *Pleurotus* and a construct comprising the promoter operably linked to a heterologous transcribable polynucleotide molecule.

However, there is a need to increase gene expression of glyceraldehyde-3-phosphate dehydrogenase promoter in basidiomycetous fungi.

SUMMARY OF THE INVENTION

One object of the invention is to provide an isolated nucleic acid comprising a basidiomycetes glyceraldehyde-3-phosphate dehydrogenase promoter wherein the fragment having the GC content higher than about 40% in 5' flanking region is deleted.

Another object of the invention is to provide a construct comprising the promoter of the invention operably linked to a heterologous transcribable polynucleotide molecule.

A further object of the invention is to provide a transformed mushroom, comprising the construct of the invention.

DETAILED DESCRIPTION OF THE INVENTION

The invention surprisingly found that partial deletion of the glyceraldehyde-3-phosphate dehydrogenase (gpd) promoter can enhance gene expression (even heterologous gene expression) in basidiomycetous fungi. With the discovery of these gpd promoters, an expression system can be constructed for the expression of a heterologous gene in mushroom.

According to the invention, the term "isolated" as used herein refers to an isolated nucleic acid molecule that, by the hand of man, exists outside its native environment and is therefore not a product of nature. An isolated nucleic acid molecule may exist in a purified form or in a non-native environment, such as a transgenic host cell.

As used herein, the term "promoter" refers to a polynucleotide molecule that in its native state is located upstream or 5' end to a translational start codon of an open reading frame (or protein-coding region) and that is involved in recognition and binding of RNA polymerase II and other proteins (trans-acting transcription factors) to initiate transcription. When operably linked to a transcribable polynucleotide molecule, a promoter typically causes the transcribable polynucleotide molecule to be transcribed in a manner that is similar to the transcription of the polynucleotide molecule that is normally associated with the promoter. The promoters of the invention can include those produced through the manipulation of known promoters to produce artificial, chimeric, or hybrid ones. Such promoters can also combine cis-elements from one or more promoters, for example, by adding a heterologous regulatory element to an active promoter with its own partial or complete regulatory elements.

As used herein, the term "operatively linked" refers to two nucleic acid sequences that are related physically or functionally. For example, a promoter or regulatory DNA sequence is said to be "associated with" a DNA sequence that codes for a RNA or a protein if the two sequences are operatively linked or so situated that the regulator DNA sequence will affect the expression level of the coding or structural DNA sequence.

As used herein, the term "transcribable polynucleotide molecule" refers to any polynucleotide molecule capable of being transcribed into a RNA molecule.

As used herein, the term "heterologous nucleic acid Sequence" refers to a nucleic acid sequence not naturally associated with the host genome into which it is introduced, including non-naturally occurring multiple copies of a naturally occurring nucleic acid sequence.

As used herein, the phrase "polynucleotide construct" refers to any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecules have been linked in a functionally operative manner. The terms "polynucleotide construct" and "construct" are used interchangeably herein.

As used herein, the term "transformed" refers to a cell, tissue, organ, or organism into which a foreign polynucleotide molecule, such as a construct, has been introduced. Preferably, the polynucleotide molecule introduced is integrated into the genomic DNA of the recipient cell, tissue, organ, or organism so that the introduced polynucleotide molecule is inherited by subsequent progeny.

As used herein, the term "expression" includes any step involved in the production of the polypeptide including, but not limited to, transcription, post-transcriptional modification, translation, post-translational modification, and secretion.

As used herein, the term "expression vector" refers to a linear or circular DNA molecule that comprises a polynucleotide encoding a polypeptide of the present invention and is operably linked to additional nucleotides that provide for its expression.

As used herein, the term "host cell" includes any cell type that is susceptible to transformation, transfection, transduction, and the like with a nucleic acid construct or expression vector comprising a polynucleotide of the present invention.

The present invention is based on the surprising finding that basidiomycetes gpd promoter may be truncated to remove a high GC content fragment in 5' flanking region thereof and the truncated gpd promoter can enhance protein expression. Accordingly, the invention provides an isolated nucleic acid comprising a basidiomycetes glyceraldehyde-3-phosphate dehydrogenase promoter wherein the fragment having the GC content higher than about 40% in 5' flanking region is deleted.

In another embodiment of the invention, the gpd promoter is from basidiomycetes. More preferably, the gpd promoter is from *Schizophyllum, Phanerochaete, Agaricus, Lentinula, Flammulina* or *Pleurotus*. More preferably, the gpd promoter is from *Schizophyllum commune, Phanerochaete chrysosporium, Agaricus bisporus, Lentinula edodes, Flammulina velutipes, Pleurotus ostreatus, Pleurotus pulmonarius* or *Pleurotus populinus*. Most preferably, the gpd promoter has the nucleic acid sequence as shown in SEQ ID NO: 1, which is an universal promoter for basidiomycetes. The sequences of SEQ ID NOs: 1 is shown as follows:

```
                                                                SEQ ID NO: 1
  1 TGGTTCGACG GGCAAGGAAG GTCAAGGCTG TACGCCCTTT GACAGCACAG AGTGTGTTGG

61 AATGACGGGT GTTACAGGTG GACTGCGCTG CGCACGATGC CAATATTCGC ATTACTTCGC

121 TCTACGATGA GGTTTTGCAC AGAACCTTAG GTCGGGTGTC GGGCCCCTGC TGACCCGAGC

181 TACTTAATAC TTTCTTTCCT TCGACTTTGC TCAAACTTAA ACGAGAGTAA GTACCGGTTC

241 TGACAGTCAC TCAATATTCG TCTGATGCTC TCTCGGGGGA AATCTCTCTC CAACGACCAT

301 TCTTTATTAT CTGAAGCTGG TTGTCTTCGA TCGAGTATAC GACGTCCTGG GGCTTGTCTT

361 AGTCTCACGA AGGCCGACTC TATCGCTCTA GGACTCGCTT GATATAGATG TGCGTAACTT

421 TAAGTGAGCT CGTATTCATC TTATTCCATT CCCATTGAGT CGTGGGTCCA GCATTTTGTT

481 CGAGAGAGTC AAGACTCGAG GATACCGCTA GTCGCCTGTG GTCTGGATCG TTCCTTCTAT

541 GTTCGGTGTC TGGAGCATGG CCTTTCTAGA CTCTTGGCTG GTACTGGACG ACCAATCACG
```

```
601 AGGTGCCTGT GGCGCACATT ATGGCTCTCC GTGTGCTCCA GCCAATTAGG TTCCGGGGAG

661 GGGTTATGCA TTAGAAACGA TCTGTTCATC TGAAAGGTGG TATCGCGTTT GTTGTGTGGA

721 TGACCACCCT AGATGAGGCC TGGATGATAC TGCCTTAAAA TTGGAGGCGC GTCCAGGGCG

781 CGTCGTTCTC CGAGTCTGTT CCGCTGATGA ATTTTGCCTG CTCGACATCG TTTCTGCGGA

841 CATGCGATCG ACGAGATCTT TGCGTTAGAC GCCGTTGGGA AGGGACTCGG AGGTGGGTTT

901 AGACCTGCGT GGTAGAAGAA TGGGACGAGT ATATGAGTAG AGTACCGCGT CGATACCGCG

961 TAACCGTGCA TGTGCTACTA CTCCTTGACC GCTGATTGGT TGCGAACTCG ACATGATCTA

1021 GGTCGTCCTC GTCTGGACTC CTAATCAAGA GAGACAAGAG AATGGTTGAG GAGCTGCTCA

1081 AATTTTGGCG GATAACGTCG TCGGTATCCT ATGAATCTAC GTTGTGTATC TCTAATGCTT

1141 TGTACGTCTT TGACGCGGTA AGAATTTAGG ACGGAATGCA GACGAAATGA CAGCGATGAC

1201 GTAACATCCG ATTATCAGCG CGACAGTATA AAAGGCGCAG AATTTTGACA TCTCTCC
```

In a preferred embodiment of the invention, the invention provides an isolated nucleic acid comprising a glyceraldehyde-3-phosphate dehydrogenase promoter comprising the nucleic acid sequence as shown in SEQ ID NO: 1, wherein the fragment having the GC content higher than about 40% in 5' flanking region is deleted.

According to the invention, the deleted fragment in 5' flanking region of gpd promoter has the GC content higher than about 44%, about 45%, about 50%, about 51%, about 52%, about 53%, about 54%, about 55% or about 56%. In one embodiment, the deleted fragment in 5' flanking region of gpd promoter has the GC content ranging from about 40% to about 75%, preferably, about 44% to about 75%, about 44% to about 70%, about 44% to about 65%, about 44% to about 60%, about 45% to about 75%, about 45% to about 70%, about 45% to about 65%, about 45% to about 60%, about 50% to about 75%, about 50% to about 70%, about 50% to about 65% or about 50% to about 60%.

In a preferred embodiment, the deleted fragment in 5' flanking region of gpd promoter has the sequence located at the position from −1256 to −626 (SEQ ID NO:4). Preferably, the deleted fragment in 5' flanking region of gpd promoter with the sequence of SEQ ID NO: 1 has the sequence located at the position selected from the group consisting of −1256 to −1149 (SEQ ID NO:2), −1256 to −791 (SEQ ID NO: 3) and −1256 to −626 (SEQ ID NO: 4) of SEQ ID NO: 1. The sequences of SEQ ID NOs: 2-4 are as follows:

```
                                                              SEQ ID NO: 2
  1 TGGTTCGACG GGCAAGGAAG GTCAAGGCTG TACGCCCTTT GACAGCACAG AGTGTGTTGG

61 AATGACGGGT GTTACAGGTG GACTGCGCTG CGCACGATGC CAATATTC
```

```
                                                              SEQ ID NO: 3
  1 TGGTTCGACG GGCAAGGAAG GTCAAGGCTG TACGCCCTTT GACAGCACAG AGTGTGTTGG

61 AATGACGGGT GTTACAGGTG GACTGCGCTG CGCACGATGC CAATATTCGC ATTACTTCGC

121 TCTACGATGA GGTTTTGCAC AGAACCTTAG GTCGGGTGTC GGGCCCCTGC TGACCCGAGC

181 TACTTAATAC TTTCTTTCCT TCGACTTTGC TCAAACTTAA ACGAGAGTAA GTACCGGTTC

241 TGACAGTCAC TCAATATTCG TCTGATGCTC TCTCGGGGGA AATCTCTCTC CAACGACCAT

301 TCTTTATTAT CTGAAGCTGG TTGTCTTCGA TCGAGTATAC GACGTCCTGG GGCTTGTCTT

361 AGTCTCACGA AGGCCGACTC TATCGCTCTA GGACTCGCTT GATATAGATG TGCGTAACTT

421 TAAGTGAGCT CGTATTCATC TTATTCCATT CCCATTGAGT CGTGGG
```

```
                                                              SEQ ID NO: 4
  1 TGGTTCGACG GGCAAGGAAG GTCAAGGCTG TACGCCCTTT GACAGCACAG AGTGTGTTGG

61 AATGACGGGT GTTACAGGTG GACTGCGCTG CGCACGATGC CAATATTCGC ATTACTTCGC

121 TCTACGATGA GGTTTTGCAC AGAACCTTAG GTCGGGTGTC GGGCCCCTGC TGACCCGAGC

181 TACTTAATAC TTTCTTTCCT TCGACTTTGC TCAAACTTAA ACGAGAGTAA GTACCGGTTC

241 TGACAGTCAC TCAATATTCG TCTGATGCTC TCTCGGGGGA AATCTCTCTC CAACGACCAT

301 TCTTTATTAT CTGAAGCTGG TTGTCTTCGA TCGAGTATAC GACGTCCTGG GGCTTGTCTT

361 AGTCTCACGA AGGCCGACTC TATCGCTCTA GGACTCGCTT GATATAGATG TGCGTAACTT

421 TAAGTGAGCT CGTATTCATC TTATTCCATT CCCATTGAGT CGTGGGTCCA GCATTTTGTT
```

-continued

```
481 CGAGAGAGTC AAGACTCGAG GATACCGCTA GTCGCCTGTG GTCTGGATCG TTCCTTCTAT

541 GTTCGGTGTC TGGAGCATGG CCTTTCTAGA CTCTTGGCTG GTACTGGACG ACCAATCACG

601 AGGTGCCTGT GGCGCACATT ATGGCTCTCC G
```

According to the embodiments of the invention, the truncated promoter is selected from the group consisting of the sequences of SEQ ID NO: 5-7. The sequences of SEQ ID NOs: 5-7 are listed as follows:

SEQ ID NO: 5

```
    GC ATTACTTCGC

121 TCTACGATGA GGTTTTGCAC AGAACCTTAG GTCGGGTGTC GGGCCCCTGC TGACCCGAGC

181 TACTTAATAC TTTCTTTCCT TCGACTTTGC TCAAACTTAA ACGAGAGTAA GTACCGGTTC

241 TGACAGTCAC TCAATATTCG TCTGATGCTC TCTCGGGGGA AATCTCTCTC CAACGACCAT

301 TCTTTATTAT CTGAAGCTGG TTGTCTTCGA TCGAGTATAC GACGTCCTGG GGCTTGTCTT

361 AGTCTCACGA AGGCCGACTC TATCGCTCTA GGACTCGCTT GATATAGATG TGCGTAACTT

421 TAAGTGAGCT CGTATTCATC TTATTCCATT CCCATTGAGT CGTGGGTCCA GCATTTTGTT

481 CGAGAGAGTC AAGACTCGAG GATACCGCTA GTCGCCTGTG GTCTGGATCG TTCCTTCTAT

541 GTTCGGTGTC TGGAGCATGG CCTTTCTAGA CTCTTGGCTG GTACTGGACG ACCAATCACG

601 AGGTGCCTGT GGCGCACATT ATGGCTCTCC GTGTGCTCCA GCCAATTAGG TTCCGGGGAG

661 GGGTTATGCA TTAGAAACGA TCTGTTCATC TGAAAGGTGG TATCGCGTTT GTTGTGTGGA

721 TGACCACCCT AGATGAGGCC TGGATGATAC TGCCTTAAAA TTGGAGGCGC GTCCAGGGCG

781 CGTCGTTCTC CGAGTCTGTT CCGCTGATGA ATTTTGCCTG CTCGACATCG TTTCTGCGGA

841 CATGCGATCG ACGAGATCTT TGCGTTAGAC GCCGTTGGGA AGGGACTCGG AGGTGGGTTT

901 AGACCTGCGT GGTAGAAGAA TGGGACGAGT ATATGAGTAG AGTACCGCGT CGATACCGCG

961 TAACCGTGCA TGTGCTACTA CTCCTTGACC GCTGATTGGT TGCGAACTCG ACATGATCTA

1021 GGTCGTCCTC GTCTGGACTC CTAATCAAGA GAGACAAGAG AATGGTTGAG GAGCTGCTCA

1081 AATTTTGGCG GATAACGTCG TCGGTATCCT ATGAATCTAC GTTGTGTATC TCTAATGCTT

1141 TGTACGTCTT TGACGCGGTA AGAATTTAGG ACGGAATGCA GACGAAATGA CAGCGATGAC

1201 GTAACATCCG ATTATCAGCG CGACAGTATA AAAGGCGCAG AATTTTGACA TCTCTCC
```

SEQ ID NO: 6

```
    TCCA GCATTTTGTT

481 CGAGAGAGTC AAGACTCGAG GATACCGCTA GTCGCCTGTG GTCTGGATCG TTCCTTCTAT

541 GTTGTGTATC TGGAGCATGG CCTTTCTAGA CTCTTGGCTG GTACTGGACG ACCAATCACG

601 AGGTGCCTGT GGCGCACATT ATGGCTCTCC GTGTGCTCCA GCCAATTAGG TTCCGGGGAG

661 GGGTTATGCA TTAGAAACGA TCTGTTCATC TGAAAGGTGG TATCGCGTTT GTTGTGTGGA

721 TGACCACCCT AGATGAGGCC TGGATGATAC TGCCTTAAAA TTGGAGGCGC GTCCAGGGCG

781 CGTCGTTCTC CGAGTCTGTT CCGCTGATGA ATTTTGCCTG CTCGACATCG TTTCTGCGGA

841 CATGCGATCG ACGAGATCTT TGCGTTAGAC GCCGTTGGGA AGGGACTCGG AGGTGGGTTT

901 AGACCTGCGT GGTAGAAGAA TGGGACGAGT ATATGAGTAG AGTACCGCGT CGATACCGCG

961 TAACCGTGCA TGTGCTACTA CTCCTTGACC GCTGATTGGT TGCGAACTCG ACATGATCTA

1021 GGTCGTCCTC GTCTGGACTC CTAATCAAGA GAGACAAGAG AATGGTTGAG GAGCTGCTCA

1081 AATTTTGGCG GATAACGTCG TCGGTATCCT ATGAATCTAC GTTGTGTATC TCTAATGCTT

1141 TGTACGTCTT TGACGCGGTA AGAATTTAGG ACGGAATGCA GACGAAATGA CAGCGATGAC

1201 GTAACATCCG ATTATCAGCG CGACAGTATA AAAGGCGCAG AATTTTGACA TCTCTCC
```

```
                                                            SEQ ID NO: 7
      TGTGCTCCA GCCAATTAGG TTCCGGGGAG

661  GGGTTATGCA TTAGAAACGA TCTGTTCATC TGAAAGGTGG TATCGCGTTT GTTGTGTGGA

721  TGACCACCCT AGATGAGGCC TGGATGATAC TGCCTTAAAA TTGGAGGCGC GTCCAGGGCG

781  CGTCGTTCTC CGAGTCTGTT CCGCTGATGA ATTTTGCCTG CTCGACATCG TTTCTGCGGA

841  CATGCGATCG ACGAGATCTT TGCGTTAGAC GCCGTTGGGA AGGGACTCGG AGGTGGGTTT

901  AGACCTGCGT GGTAGAAGAA TGGGACGAGT ATATGAGTAG AGTACCGCGT CGATACCGCG

961  TAACCGTGCA TGTGCTACTA CTCCTTGACC GCTGATTGGT TGCGAACTCG ACATGATCTA

1021  GGTCGTCCTC GTCTGGACTC CTAATCAAGA GAGACAAGAG AATGGTTGAG GAGCTGCTCA

1081  AATTTTGGCG GATAACGTCG TCGGTATCCT ATGAATCTAC GTTGTGTATC TCTAATGCTT

1141  TGTACGTCTT TGACGCGGTA AGAATTTAGG ACGGAATGCA GACGAAATGA CAGCGATGAC

1201  GTAACATCCG ATTATCAGCG CGACAGTATA AAAGGCGCAG AATTTTGACA TCTCTCC
```

According to the invention, the truncated promoter of the invention can be obtained by using general technology in molecular biology such as cloning, PCR amplification and plasmid constructions etc.

Methods well known to one skilled in the art may be used to identify promoters of interest having activity similar to the promoters described herein. For example, cDNA libraries may be constructed by using cells or tissues of interest and screening them to identify genes having an expression pattern similar to that of the promoters described herein. The cDNA sequence for the identified gene may then be used to isolate the gene's promoter for further characterization. Alternately, transcriptional profiling or electronic northern techniques may be used to identify genes having an expression pattern similar to that of the promoters described herein. Once these genes have been identified, their promoters may be isolated for further characterization. The electronic northern technique refers to a computer-based sequence analysis which allows sequences from multiple cDNA libraries to be compared electronically on the basis of parameters identified by the researcher including abundance in EST populations in multiple cDNA libraries. The transcriptional profiling technique is a high-throughput method used for the systematic monitoring of gene expression profiles for thousands of genes. This DNA chip-based technology arrays thousands of cDNA sequences on a support surface. These arrays are simultaneously hybridized to a population of labeled cDNA probes prepared from RNA samples of different cell or tissue types, allowing direct comparative analysis of expression. This approach may be used for the isolation of regulatory sequences such as promoters associated with those genes.

In another embodiment, the truncated promoter disclosed herein can be modified. Those skilled in the art can create promoters that have variations in the polynucleotide sequence. The polynucleotide sequences of the promoters of the present invention may be modified or altered to enhance their control characteristics. One preferred method of alteration of a polynucleotide sequence is to use PCR to modify selected nucleotides or regions of sequences. These methods are well known to those of skill in the art. Variant promoters can be produced, for example, by standard DNA mutagenesis techniques or by chemically synthesizing the variant promoter or a portion thereof.

Novel chimeric promoters can be designed or engineered by a number of methods. For example, a chimeric promoter may be produced by fusing a first promoter fragment to a second promoter fragment; the resultant chimeric promoter may cause an increase in expression of an operably linked transcribable polynucleotide molecule. Promoters can be constructed so that promoter fragments or elements are operably linked, for example, by placing such a fragment upstream of a minimal promoter. Methods for construction of chimeric and variant promoters of the present invention include, but are not limited to, combining control elements of different promoters or duplicating portions or regions of a promoter. Those of skill in the art are familiar with the standard resource materials that describe specific conditions and procedures of the construction, manipulation, and isolation of macromolecules (e.g., polynucleotide molecules, plasmids, etc.), as well as the generation of recombinant organisms and the screening and isolation of polynucleotide molecules.

The invention also provides a construct comprising the promoter of the invention operably linked to a heterologous transcribable polynucleotide molecule. Preferably, the transcribable polynucleotide molecule is operably linked to a 3' transcription termination polynucleotide molecule.

Constructs of the present invention would typically contain a promoter operably linked to a transcribable polynucleotide molecule operably linked to a 3' transcription termination polynucleotide molecule. In addition, constructs may include but are not limited to additional regulatory polynucleotide molecules from the 3'-untranslated region (3' UTR) of the *pleurotus* genes. Constructs may also include but are not limited to the 5' untranslated regions (5' UTR) of an mRNA polynucleotide molecule which can play an important role in translation initiation and can also be a genetic component in a mushroom expression construct. These additional upstream and downstream regulatory polynucleotide molecules may be derived from a source that is native or heterologous with respect to the other elements present on the promoter construct.

Thus, constructs of the present invention comprise promoters operatively linked to a transcribable polynucleotide molecule so as to direct transcription of said transcribable polynucleotide molecule at a desired level or in a desired cell.

According to the invention, any suitable heterologous gene can be used as the heterologous transcribable polynucleotide molecule of the invention. Exemplary transcribable polynucleotide molecules for incorporation into constructs of the present invention include, but are not limited to those encoding a) antibodies, including other diagnostic material; b) secondary metabolites, such as lectins; c) therapeutic compounds such as vaccines and steroids; d) biological macromolecules, such as interferon, endostatin and insulin; e) medical enzymes, such as thrombolytics and cerebrosidases; f) genes that confer resistance to pests, disease, or herbicide, such as pesticidal compounds *Bacillus thuringiensis* protein (Bt toxin); g) genes that confer or contribute to a value-added trait, such as modification of nutrient composition or metabolism. Thus, in one preferred embodiment, a polynucleotide molecule of the present invention or fragments, variants, or derivatives thereof, capable of regulating transcription, is operably linked to a transcribable polynucleotide molecule that provides a selectable, screenable, or scorable marker. Markers for use in the practice of the present invention include, but are not limited to, transcribable polynucleotide molecules encoding glucuronidase (GUS), green fluorescent protein (GFP), luciferase (LUC), and proteins that confer antibiotic resistance.

Methods are known to introduce constructs of the invention into a cell in such a manner that the transcribable polynucleotide molecule is transcribed into a functional mRNA molecule that is translated and therefore expressed as a protein product. For the practice of the present invention, conventional compositions and methods for preparing and using constructs and host cells are well known to one skilled in the art. Introducing recombinant molecules into cells involve mechanical means such as direct DNA uptake, liposomes, electroporation (Guerche, P. et al.), microinjection (Neuhaus, G. et al.), and use of microprojectiles and a gun or other device to force small particles coated with DNA into cells (Klein, T. M. et al.).

A further object of the invention is to provide a transformed mushroom containing the construct of the invention.

A transformation construct containing a promoter of the present invention may be introduced into mushrooms by any transformation method. Methods and materials for transforming mushrooms by introducing a mushroom expression construct into a mushroom genome in the practice of this invention can include any of the well-known and demonstrated methods including electroporation, *Agrobacterium*-mediated transformation and protoplast transformation. Preferably, the mushroom is selected from the group consisting of *Flammulina, Agaricus, Pleurotus* and *Lentinula*. More preferably, the mushroom is selected from the group consisting of *Pleurotus ostreatus, Pleurotus pulmonarius,* and *Pleurotus populinus*. Most preferably, the mushroom is *Pleurotus ostreatus*.

The deletion of the fragments of the 5'-flanking region of gpd promoter would lead to higher heterologous gene expression. The partial deletion of gpd promoter provides a feasible strategy in enhancement of heterologous gene expression. According to the invention, the heterologous gene expression level driven by the partial deleted gpd promoter of the present invention is elevated to at least about 500-fold, 1000-fold, 2000-fold, 3000-fold, 4000-fold or 5000-fold as compared to that by the full-length gpd promoter.

The following examples are included to demonstrate preferred embodiments of the present invention. It should be appreciated by those of skill in the art that the techniques disclosed in the examples that follow represent techniques discovered by the inventors to function well in the practice of the present invention. However, those of skill in the art should, in light of the present disclosure, appreciate that many changes can be made in the specific embodiments that are disclosed and still obtain a similar result without departing from the spirit and scope of the present invention. Therefore all matter set forth or shown in the accompanying drawings is to be interpreted as illustrative and not limiting.

EXAMPLE

Example 1

Construction of Plasmid Containing Truncated Promoters

Strains and Media

*F. velutipes* BCRC 37086, purchased from the Bioresources Collection and Research Center (Hsinchu, Taiwan), was grown and maintained on CYM agar or broth (Difco, Detroit, Mich.) at 25° C. *Escherichia coli* DH5α, used for DNA manipulation and plasmid conservation, was grown in LB medium (Sigma, St Louis, Mo.) at 37° C. *Agrobacterium tumefaciens* strain LBA4404, kindly provided by Dr. Yee-Yung Charng, Agricultural Biotechnology Research Center, Academia Sinica (Taipei, Taiwan), was used for transformation and grown in LB medium at 28° C.

Fruiting of *F. velutipes*

A substrate composed of 65% sawdust and 35% rice bran was placed into a polypropylene bottle and autoclaved for 1 h. Capped bottles with substrates were inoculated with mycelial plugs and incubated at 23° C. for 3 to 4 weeks. After bottles were completely colonized by the mycelia, mushroom fruiting was induced by water addition and temperature shift from 23 to 10° C.

Plasmid Construction

The backbone plasmid, p0390-AH, harboring *E. coli* hygromycin B phosphotransferase (hph) under control of the gpd promoter from *A. bisporus*, was constructed by inserting pGPD-hph cassette (Kuo et al., 2004) into pCAMBIA0390. The *F. velutipes* gpd promoter with 1257 bp in length was truncated according to the site of CAAT box. The truncated gpd promoters with various length in 5'-upstream region were named as PgpdΔd1 (1149 bp), PgpdΔd2 (791 bp), PgpdΔd3 (626 bp) and PgpdΔd4 (248 bp), respectively. Enhanced green fluorescent protein (egfp) gene, driven by *F. velutipes* full-length or partially truncated gpd promoters with its first intron, were inserted into p0390-AH, and the resulting plasmids were designated as pFiegfp, pFiegfpΔd1, pFiegfpΔd2, pFiegfpΔd3 and pFiegfpΔd4, respectively. The designation of promoters and corresponding plasmids are showed in Table 1.

TABLE 1

The designation of deleted promoter fragment for corresponding plasmids and generated transformants

| Promoter | Deleted fragment | Transferred plasmid | Transformant |
|---|---|---|---|
| Pgpd | — | pFiegfp | D0 |
| Pgpd Δ1 | d1 (108 bp) | pFiegfp Δd1 | D1 |
| Pgpd Δ2 | d2 (466 bp) | pFiegfp Δd2 | D2 |
| Pgpd Δ3 | d3 (631 bp) | pFiegfp Δd3 | D3 |
| Pgpd Δ4 | d4 (1009 bp) | pFiegfp Δd4 | D4 |

Example 2

*Agrobacterium*-Mediated Transformation

Transformation of *F. velutipes*

*Agrobacterium*-mediated transformation was performed as described by Chen et al. (Chen et al., 2000) with minor modification. All expression vectors were introduced into *A. tumefaciens* by electroporation. The *A. tumefaciens* harbouring target plasmid was cultivated overnight in LB containing 50 μg/ml kanamycin with shaking at 220 rpm, followed by mixing with *F. velutipes* modified mycelia pellet (MMP) in induction medium (IM) which containing 200 μM acetosyringone (AS) for 6 h. The MMPs were subsequently transferred to fresh medium for 5 days. The MMP was then thoroughly washed and transferred to CYM plate containing 30 μg/ml hygromycin B and 200 μM cefotoxime, and incubated at 23° C. till the mycelia grew. The *F. velutipes* containing pFiegfp, pFiegfpΔd1, pFiegfpΔd2, pFiegfpΔd3 and pFiegfpΔd4 are named as D0, D1, D2, D3 and D4 transformants.

Figure 1:
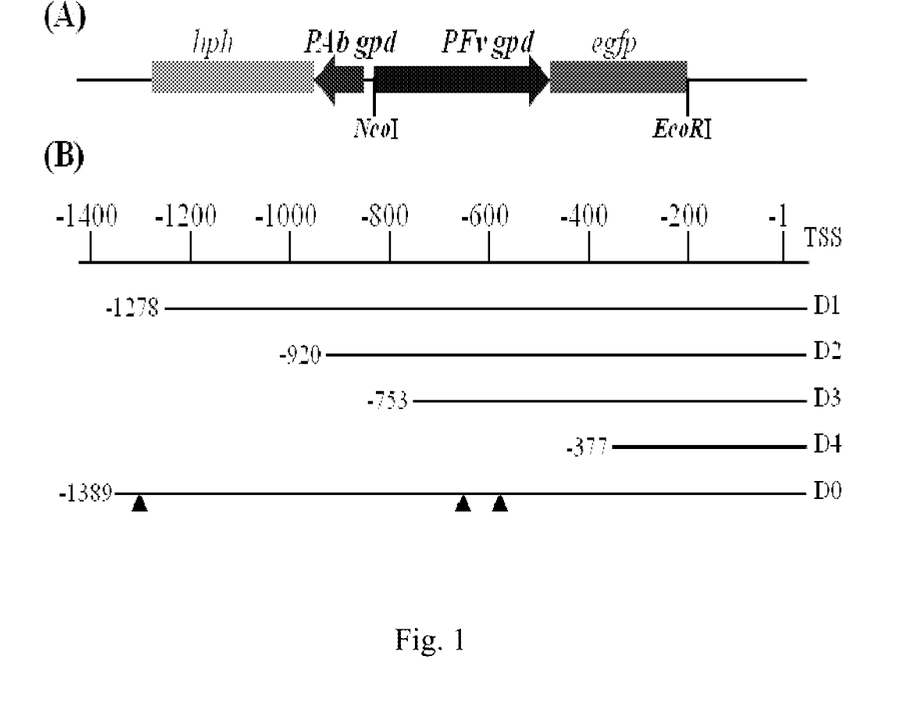
FIG. 1 shows that *F. velutipes* gpd promoter is totally 1256 bp in length. The grey shading area implies three CAAT boxes; Located palindrome sequences are symbolized with two-way arrow heads; Leftwards arrow with dotted line indicates each deleted fragments d1 to d4.
Figure 2:
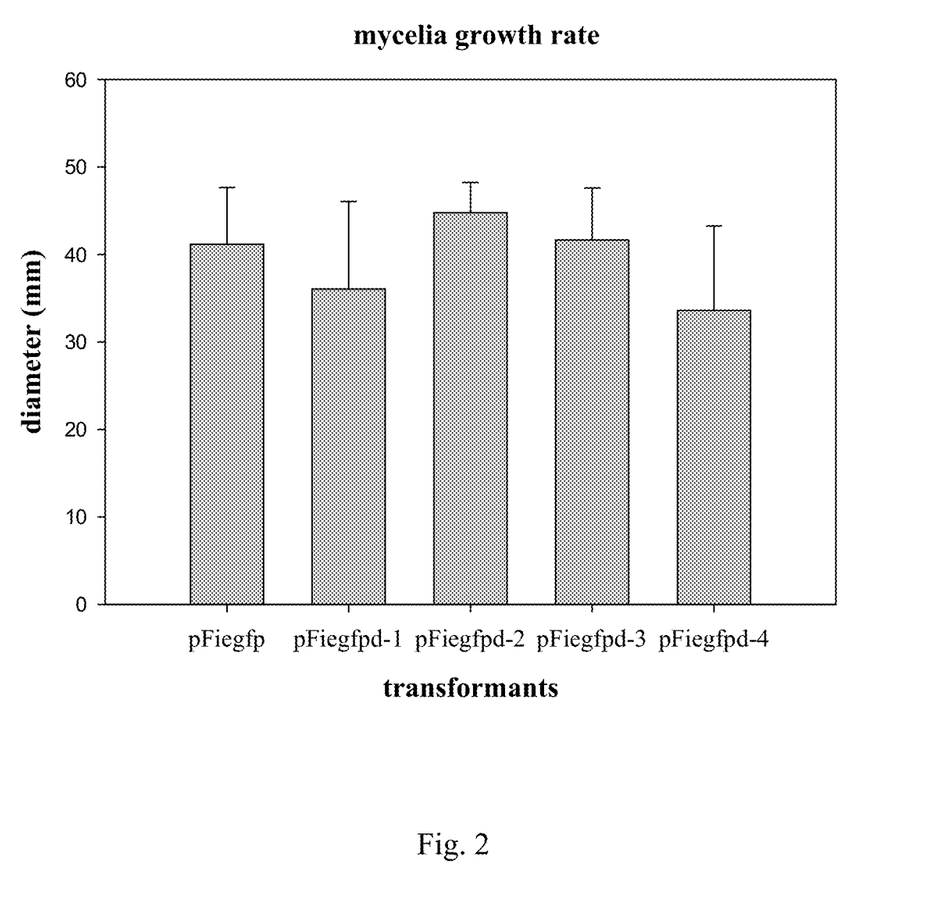
FIG. 2 shows growth rate of transformants with different length of gpd promoter.

Plasmids with different length of gpd promoters, pFiegfp, pFiegfpΔd1 to pFiegfpΔd4 were introduced into *A. tumefaciens* by electroporation, and confirmed by colony PCR using corresponding primers. After co-cultivating with the *A. tumefaciens* containing pFiegfp series plasmids under the selection pressure for four weeks, the *F. velutipes* MMP were transferred to fresh medium with 30 μg/mL hygromycin B. At least 30% of transformation efficiency was achieved using different plasmids via ATMT. In order to prevent the false positive result, all putative transformants were subcultured on fresh selective medium three times to confirm gene integration. The resultant transformants were subsequently transferred to fresh agar plates with selective pressure, and their growth rates assayed by the diameter of mycelia are shown in FIG. 2. No significant difference was found in growth rate between gpd promoters in different length.

Example 3

Verification of EGFP Gene Insertion

Genomic DNA PCR and Southern Blotting

Genomic PCR and Southern blotting were used to confirm the gene integration of hph and egfp into the chromosome of *F. velutipes* transformants. The genomic DNA was extracted from four-week-old mycelia grow in CYM broth with 30 μg/ml hygromycin B by using Genomic DNA mini kit (Geneaid, Taipei, Taiwan).

The Southern blotting was carried out based on the method of Kuo et al. (Kuo et al., 2004). Briefly, 10 μg of *F. velutipes* genomic DNA was digested with restriction enzymes NcoI and BamHI, separated by 0.8% agarose gel and vacuum transferred to Immobilon-Ny+ transfer membrane (Millipore, Billerica, Mass.). Egfp probe was generated by using primer EGFP-F (5'-ATGGTGAGCAAGG-3') (SEQ ID NO:5) and EGFP-R (5'-TACTTGTACAGCTCGTCCA-3') (SEQ ID NO:6), while the primer set, hph-F (ATGAAAAAGCCTGAACTCACC) (SEQ ID NO:7) and hph-R, (ACAACTTAATAA-CACATTGCG) (SEQ ID NO:8) was used for hph probe. Subsequent probe labelling, hybridization, and signal detection were conducted by means of the digoxigenin (DIG)-probe synthesis and detection kit (Roche, Mannheim, Germany) according to the manufacturer's instructions.

Figure 3:
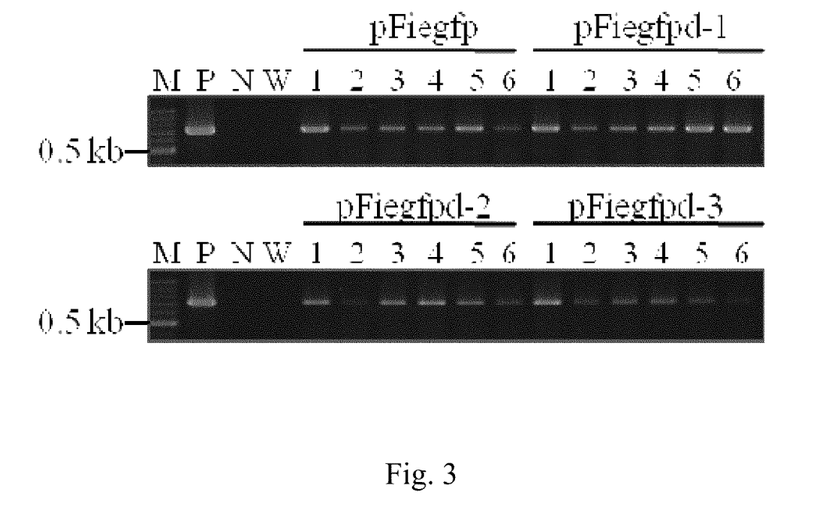
FIG. 3 shows electrophoresis of genomic DNA PCR products. By using egfp specific primer, the sizes of generated PCR products were about 720 bp. P, N: positive and negative control; W: wild type *F. velutipes*.
Figure 4:
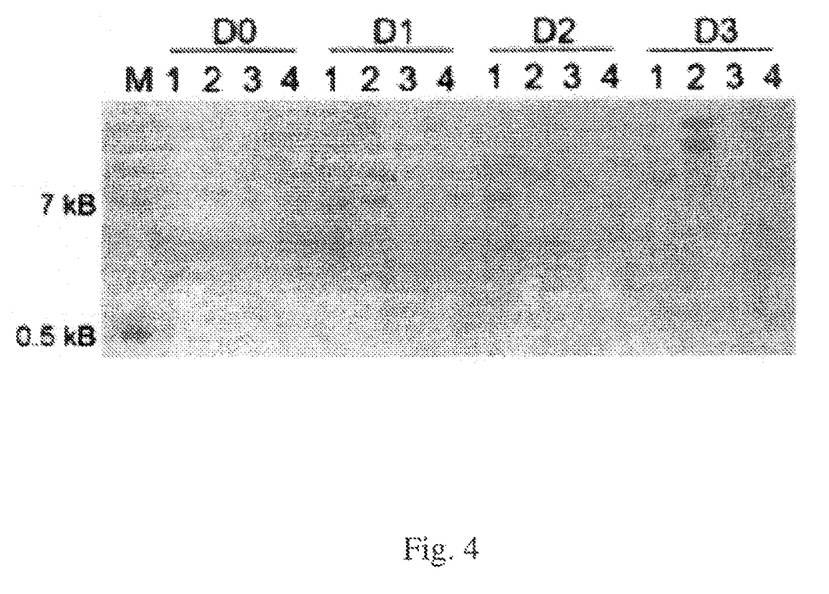
FIG. 4 shows results of southern blotting. 10 µg of transformants genomic DNA were digested by NcoI and BamHI. Transformants D0 to D3 were analyzed, each pattern indicate one to two copy numbers.

To minimize the variation resulted from the antibiotic selection, the hygromycin resistance trait in all plasmids was driven by *A. bisporus* gpd promoter constitutively. After selection, the presence of EGFP gene driven by the *F. velutipes* gpd promoter with various lengths was checked by genomic PCR. A fragment of 720 bp indicated the insertion of egfp among all putative transformants (FIG. 3). No false positives were detected by PCR amplification among 24 antibiotic resistant cultures. In order to investigate the fate of transforming DNA, Southern blotting analysis was performed. FIG. 4 shows that the egfp gene integrated one or two copies in tested transformants, and bands of various sizes were visualized. This result suggested that the introduced fragment was integrated randomly into the *F. velutipes* genome.

Example 3

Detection of EGFP in Transformants

Figure 5:
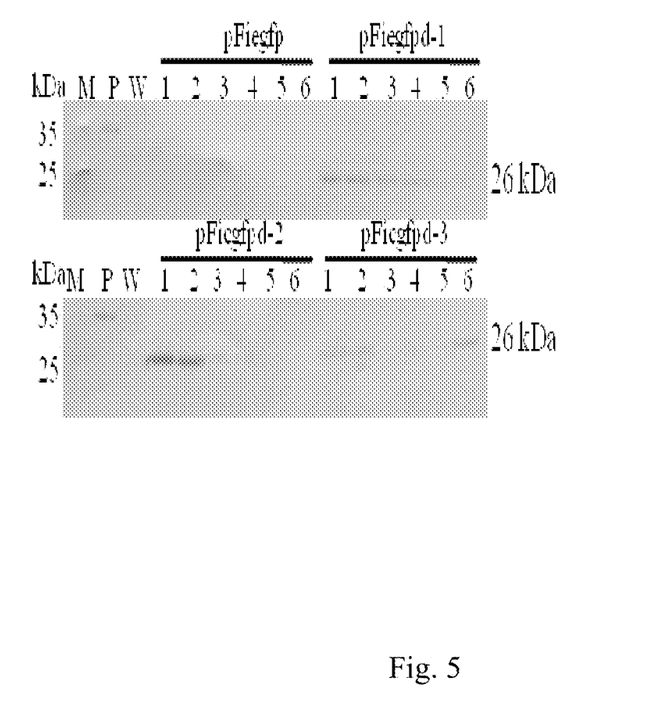
FIG. 5 shows western blot analysis of D1 to D4 transformants. *E. coli* derived recombinant EGFP was served for positive control (PC), while the negative control was from the total soluble protein of wild type *F. velutipes*. The others were D0 to D3, as indicated.

The expression of egfp was confirmed by western hybridization as shown in FIG. 5. Immunoblotting with the monoclonal anti-GFP antibody detected 27-kDa bands in positive control (PC) and total cellular protein of D1, D2 and D3 transformants, while D4 transformant showed no signal (data not shown).

Figure 6:
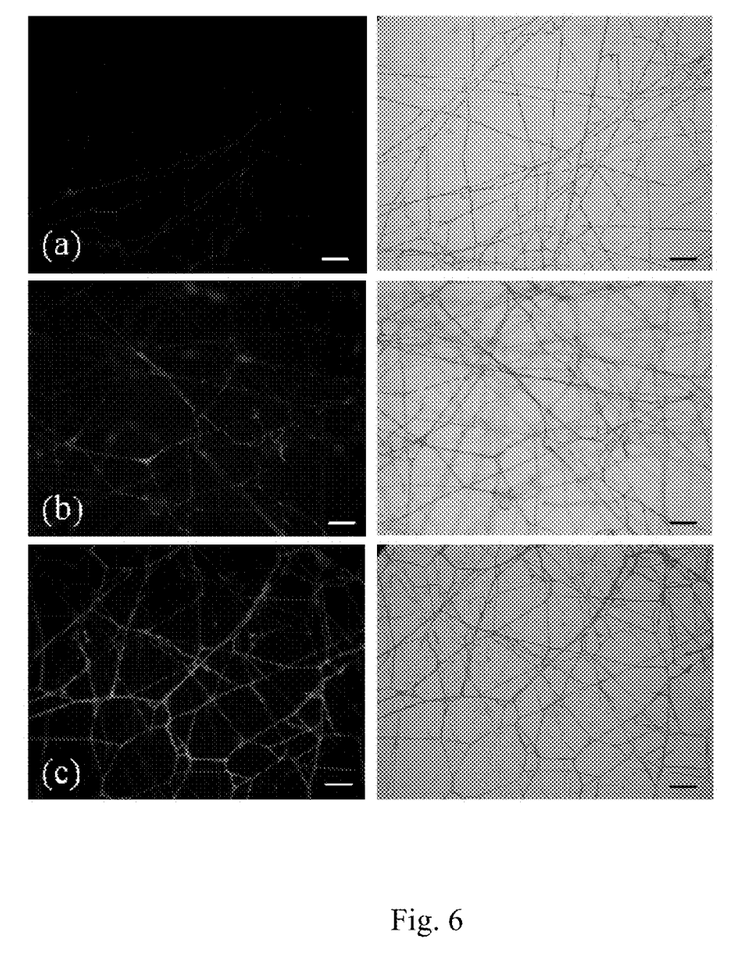
FIG. 6 shows results of transformants screened by fluorescent microscopy. With the same microscope equipment of a excitation filters at 450-490 nm, a dichroic filter at 505 nm and an emission filter at 520 nm. Images were taken with 40 folds fields of view. (A) *F. velutipes* wild type mycelia were examined using bright-field microscopy (right) and epi-fluorescence (left). The D1 (C) transformants showed strong fluorescent intensity, when comparing to the transformants carried full-length gpd promoter, D0 (B). Bar=50 µm

The mycelia of putative transformants were examined by a fluorescent microscope (Eclipse E600, Nikon, Tokyo, Japan) using a Nikon B-2A filter (excitation filter, 450-490 nm; dichroic filter, 505 nm; barrier filter, 520 nm). An in vivo imaging system (IVIS) Spectrum (Caliper Life Sciences, Hopkinton, Mass.) was used to visualize the fruiting bodies. FIG. 6 shows the fluorescent microphotographs of mycelia of wild type, D0 and D1 transformants. In comparison with D0, the D1 showed more intensive fluorescence under the same exposure conditions. However, no obvious fluorescence was observed in D4 (data not shown) which was in agreement with the western blotting analysis.

Figure 7:
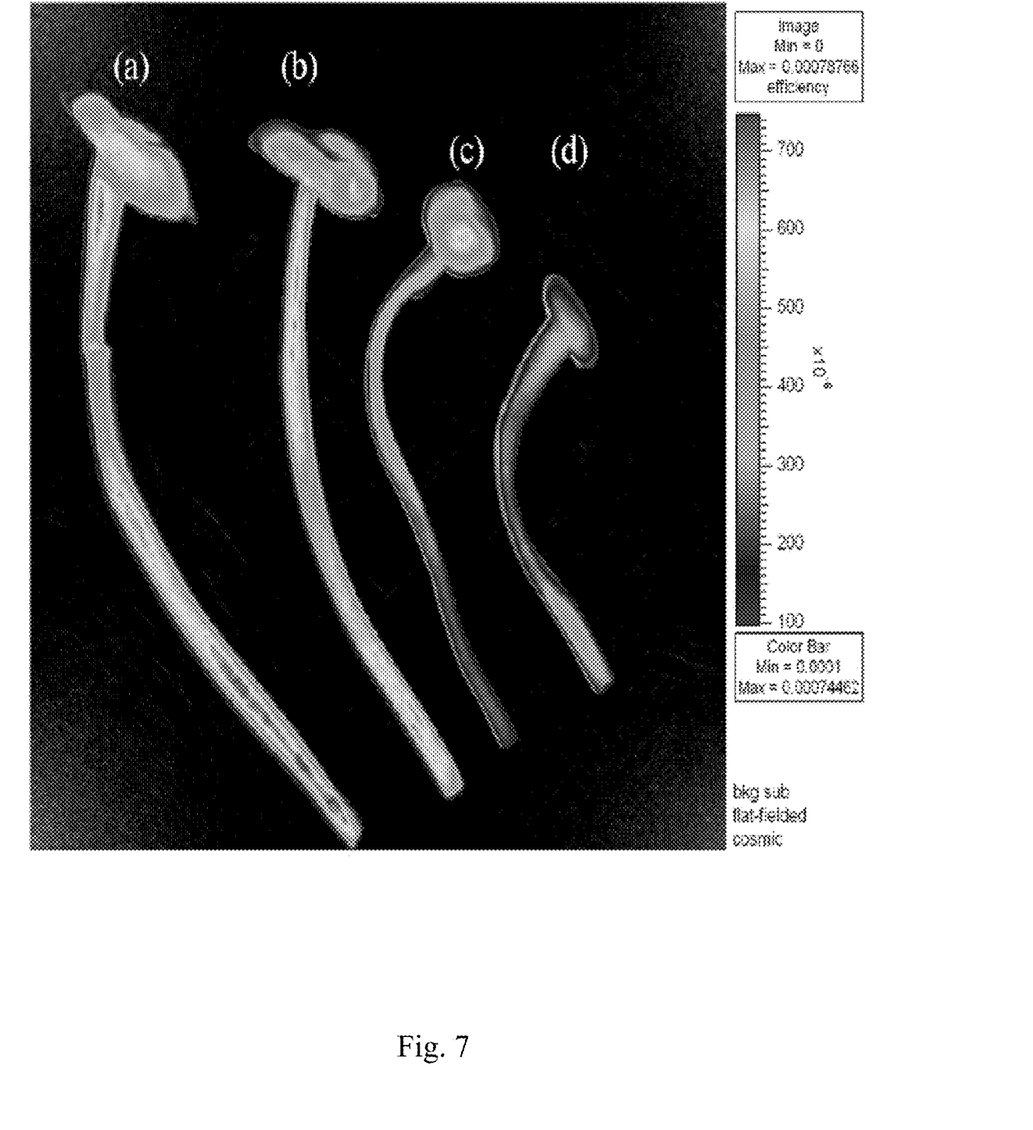
FIG. 7 shows fruiting body of *F. velutipes* evaluated by IVIS spectrum. Transformants D1 (a) and D3 (b) can be discriminated from the wild type (d) by the fluorescent intensity as indicated in the photograph, while the full-length transformant (c) showed lower epi-fluorescence than the truncated one.

The selected dikaryotic mycelia were inoculated into the sawdust medium for fruiting body development. After 6-8 weeks of induction by low temperature, all transformants had fructified successfully. The fruiting bodies of *F. velutipes* wild type, D0, D1 and D3 were observed by IVIS as illustrated in FIG. 7. The D1 and D3 showed more intensive fluorescence than D0, while only autofluorescence was observed in wild type fruiting body. The EGFP fluorescence was located mainly in mushroom cap, especially the gill tissue.

Example 4

EGFP Expression Level in *F. velutipes* Mycelia

Mycelia were collected and subsequently ground in liquid nitrogen with a mortar and pestle. A total of 50 mg mycelial powder was mixed with 1 ml protein extraction buffer (50 mM sodium phosphate, 300 mM NaCl, 1 mM PMSF, 0.1% Triton X-100, pH 7.4) on ice for a period of 1 h. After centrifuging at 13,000 g for 20 min, supernatant was collected as total soluble protein. A sandwich ELISA for EGFP was performed on 100 μl of each protein extract. Samples were incubated for 1 h on ELISA plates (PerkinElmer, Boston, Mass.) coated with monoclonal EGFP antibody (ab1218, Abcam, Cambridge, UK). The assay of each sample was repeated in triplicate for each plate. Rabbit anti-GFP polyclonal antibody (ab6556, Abcam) was added to each well at a 1:10,000 dilution and incubated for 1 h at 4° C. Goat polyclonal antibodies against rabbit IgG conjugated to HRP enzyme (PerkinElmer) were added to each well at a 1:5,000 dilution and incubated for 1 h at 4° C. To each well, 100 μl of TMB-HRP microwell substrate (BioFX, Owings Mills, Md.) was added. After 5 min, the absorbance at 650 nm in each well was measured using a 96-well plate reader (VERSAmax, Sunnyvale, Calif.). Protein concentrations were determined using the BCA Assay Kit (Pierce, Rockford, Ill.). The EGFP expressed in *E. coli* BL21 (DE3) by pET21a(+) was used as a standard.

Figure 8:
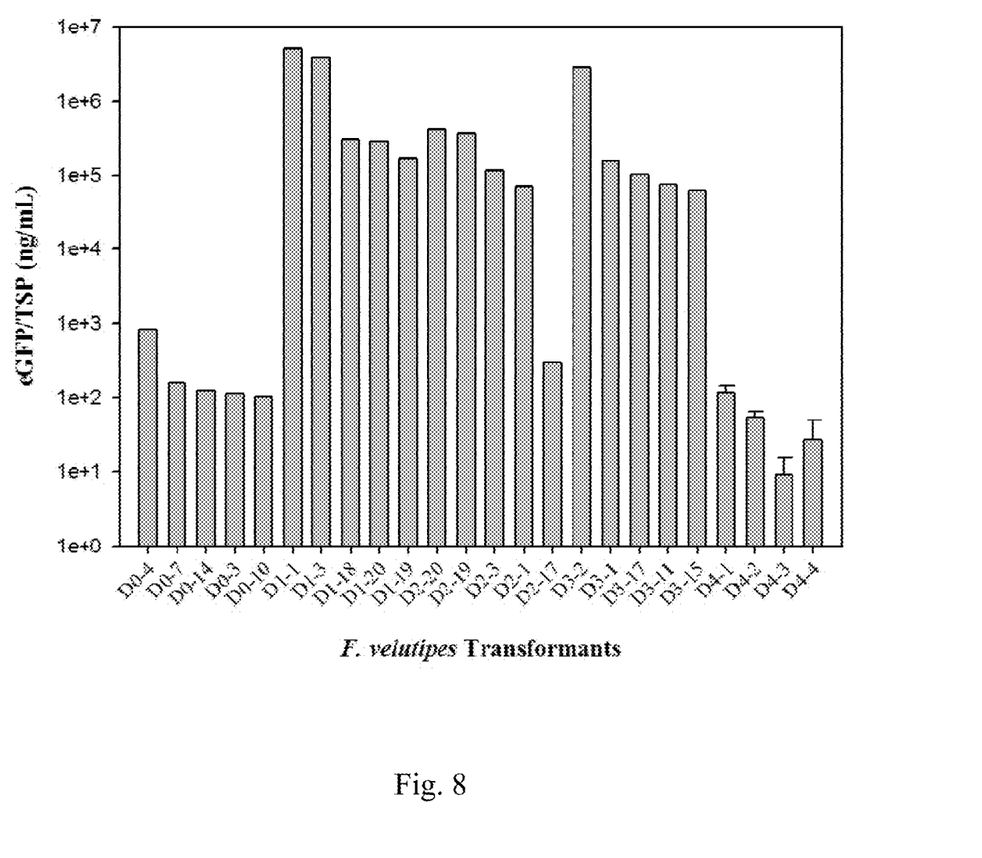
FIG. 8 shows the result of egfp protein quantification. EGFP expression amount of each group with different promoter length was measured by indirect sandwich ELISA method. The front five were transformants with full length gpd promoter (D0), followed by series of D1 to D4 transformants.

Transformants confirmed by fluorescent detection were chosen for EGFP assay. Mycelia of randomly selected transformants for D0, D1, D2, D3 and D4 were washed free of medium, frozen and ground into fine powder, followed by protein extraction. FIG. 8 shows the EGFP production of the top five transformants from each construction. The EGFP production of D1, D2 and D3 transformants could reach 0.84±0.04, 5136.66±35.02 and 409.66±21.22 µg/g total soluble protein (TSP), respectively. In contrast, there was only 0.12±0.03 µg/g TSP in average for the D0 transformants. Sequence analysis shows that the deleted fragment of D1 exhibited the highest proportion of GC nucleotides. A high GC content fragment with corresponding Gibb's free energy is prone to form secondary structure. Furthermore, there exists 3 palindrome sequences in the deleted fragment of gpd-D1 had reinforce the possibility of forming secondary structure, hence constrain the gene expression.

What is claimed is:

1. A construct comprising a truncated basidiomycetes glyceraldehyde-3-phosphate dehydrogenase (gpd) promoter consisting of a sequence selected from the group consisting of SEQ ID NO: 5, 6 or 7 and a heterologous transcribable polynucleotide molecule, wherein the promoter is operably linked to the heterologous transcribable polynucleotide molecule.

2. The construct of claim 1, wherein the transcribable polynucleotide molecule is operably linked to a 3' transcription termination polynucleotide molecule.

3. The construct of claim 1, wherein said transcribable polynucleotide molecule is a gene encoding an antibody, a therapeutic compound, a biological macromolecule, a medical enzyme; a gene that confers resistance to a pest, a disease, or a herbicide; or a gene that confers or contributes to a value-added trait.

4. The construct of claim 3, wherein said therapeutic compound is a vaccine, said biological macromolecule is an interferon, lectin, endostatin or insulin, said medical enzyme is thrombolytic or cerebrosidase and said gene that confers resistance to a pest, a disease or a herbicide encodes a *Bacillus thuringiensis* protein.

5. The construct of claim 1, wherein said transcribable polynucleotide molecule is a marker gene.

6. The construct of claim 1, wherein said transcribable polynucleotide molecule is a green fluorescence protein gene.

7. A transformed cell, comprising the construct of claim 1.

8. A transformed mushroom, comprising the construct of claim 1.

9. The transformed mushroom of claim 8, wherein the mushroom is selected from the group consisting of *Flammulina*, *Agaricus*, *Pleurotus* and *Lentinula*.

10. The transformed mushroom of claim 8, wherein the mushroom is selected from the group consisting of *Schizophyllum commune*, *Phanerochaete chrysosporium*, *Agaricus bisporus*, *Lentinula edodes*, *Flammulina velutipes*, *Pleurotus ostreatus*, *Pleurotus pulmonarius* and *Pleurotus populinus*.

11. The transformed mushroom of claim 8, wherein the mushroom is *Flammulina velutipe*.

12. A method of directing expression of a transcribable polynucleotide molecule comprising transforming a mushroom cell with the construct of claim 1 and expressing the transcribable polynucleotide molecule.

* * * * *

SEQUENCE LISTING

<160> NUMBER OF SEQ ID NOS: 11

<210> SEQ ID NO 1
<211> LENGTH: 1257
<212> TYPE: DNA
<213> ORGANISM: Basidiomycetes

<400> SEQUENCE: 1

```
tggttcgacg ggcaaggaag gtcaaggctg tacgcccttt gacagcacag agtgtgttgg      60
aatgacgggt gttacaggtg gactgcgctg cgcacgatgc caatattcgc attacttcgc     120
tctacgatga ggttttgcac agaaccttag gtcgggtgtc gggcccctgc tgacccgagc     180
tacttaatac tttctttcct tcgactttgc tcaaacttaa acgagagtaa gtaccggttc     240
tgacagtcac tcaatattcg tctgatgctc tctcggggga aatctctctc caacgaccat     300
tctttattat ctgaagctgg ttgtcttcga tcgagtatac gacgtcctgg ggcttgtctt     360
agtctcacga aggccgactc tatcgctcta ggactcgctt gatatagatg tgcgtaactt     420
taagtgagct cgtattcatc ttattccatt cccattgagt cgtgggtcca gcattttgtt     480
cgagagagtc aagactcgag gataccgcta gtcgcctgtg gtctggatcg ttccttctat     540
gttcggtgtc tggagcatgg cctttctaga ctcttggctg gtactggacg accaatcacg     600
aggtgcctgt ggcgcacatt atggctctcc gtgtgctcca gccaattagg ttccggggag     660
gggttatgca ttagaaacga tctgttcatc tgaaaggtgg tatcgcgttt gttgtgtgga     720
tgaccaccct agatgaggcc tggatgatac tgccttaaaa ttggaggcgc gtccagggcg     780
cgtcgttctc cgagtctgtt ccgctgatga attttgcctg ctcgacatcg tttctgcgga     840
catgcgatcg acgagatctt tgcgttagac gccgttggga agggactcgg aggtgggttt     900
agacctgcgt ggtagaagaa tgggacgagt atatgagtag agtaccgcgt cgataccgcg     960
taaccgtgca tgtgctacta ctccttgacc gctgattggt tgcgaactcg acatgatcta    1020
ggtcgtcctc gtctggactc ctaatcaaga gagacaagag aatggttgag gagctgctca    1080
aattttggcg gataacgtcg tcggtatcct atgaatctac gttgtgtatc tctaatgctt    1140
tgtacgtctt tgacgcggta agaatttagg acggaatgca gacgaaatga cagcgatgac    1200
gtaacatccg attatcagcg cgacagtata aaaggcgcag aattttgaca tctctcc       1257
```

<210> SEQ ID NO 2
<211> LENGTH: 108
<212> TYPE: DNA
<213> ORGANISM: Basidiomycetes

<400> SEQUENCE: 2

```
tggttcgacg ggcaaggaag gtcaaggctg tacgcccttt gacagcacag agtgtgttgg      60
aatgacgggt gttacaggtg gactgcgctg cgcacgatgc caatattc                 108
```

<210> SEQ ID NO 3
<211> LENGTH: 466
<212> TYPE: DNA
<213> ORGANISM: Basidiomycetes

<400> SEQUENCE: 3

```
tggttcgacg ggcaaggaag gtcaaggctg tacgcccttt gacagcacag agtgtgttgg    60
aatgacgggt gttacaggtg gactgcgctg cgcacgatgc caatattcgc attacttcgc   120
tctacgatga ggttttgcac agaaccttag gtcgggtgtc gggcccctgc tgacccgagc   180
tacttaatac tttctttcct tcgactttgc tcaaacttaa acgagagtaa gtaccggttc   240
tgacagtcac tcaatattcg tctgatgctc tctcggggga aatctctctc caacgaccat   300
tctttattat ctgaagctgg ttgtcttcga tcgagtatac gacgtcctgg ggcttgtctt   360
agtctcacga aggccgactc tatcgctcta ggactcgctt gatatagatg tgcgtaactt   420
taagtgagct cgtattcatc ttattccatt cccattgagt cgtggg                  466

<210> SEQ ID NO 4
<211> LENGTH: 631
<212> TYPE: DNA
<213> ORGANISM: Basidiomycetes

<400> SEQUENCE: 4
tggttcgacg ggcaaggaag gtcaaggctg tacgcccttt gacagcacag agtgtgttgg    60
aatgacgggt gttacaggtg gactgcgctg cgcacgatgc caatattcgc attacttcgc   120
tctacgatga ggttttgcac agaaccttag gtcgggtgtc gggcccctgc tgacccgagc   180
tacttaatac tttctttcct tcgactttgc tcaaacttaa acgagagtaa gtaccggttc   240
tgacagtcac tcaatattcg tctgatgctc tctcggggga aatctctctc caacgaccat   300
tctttattat ctgaagctgg ttgtcttcga tcgagtatac gacgtcctgg ggcttgtctt   360
agtctcacga aggccgactc tatcgctcta ggactcgctt gatatagatg tgcgtaactt   420
taagtgagct cgtattcatc ttattccatt cccattgagt cgtgggtcca gcattttgtt   480
cgagagagtc aagactcgag gataccgcta gtcgcctgtg gtctggatcg ttccttctat   540
gttcggtgtc tggagcatgg cctttctaga ctcttggctg gtactggacg accaatcacg   600
aggtgcctgt ggcgcacatt atggctctcc g                                  631

<210> SEQ ID NO 5
<211> LENGTH: 1149
<212> TYPE: DNA
<213> ORGANISM: Basidiomycetes

<400> SEQUENCE: 5
gcattacttc gctctacgat gaggttttgc acagaacctt aggtcgggtg tcgggcccct    60
gctgacccga gctacttaat actttctttc cttcgactttt gctcaaactt aaacgagagt   120
aagtaccggt tctgacagtc actcaatatt cgtctgatgc tctctcgggg gaaatctctc   180
tccaacgacc attctttatt atctgaagct ggttgtcttc gatcgagtat acgacgtcct   240
ggggcttgtc ttagtctcac gaaggccgac tctatcgctc taggactcgc ttgatataga   300
tgtgcgtaac tttaagtgag ctcgtattca tcttattcca ttcccattga gtcgtgggtc   360
cagcattttg ttcgagagag tcaagactcg aggataccgc tagtcgcctg tggtctggat   420
cgttccttct atgttcggtg tctggagcat ggcctttcta gactcttggc tggtactgga   480
cgaccaatca cgaggtgcct gtggcgcaca ttatggctct ccgtgctctc agccaattaa   540
ggttccgggg aggggttatg cattagaaac gatctgttca tctgaaaggt ggtatcgcgt   600 tgttgtgtg gatgaccacc ctagatgagg cctggatgat actgccttaa aattggaggc   660
gcgtccaggg cgcgtcgttc tccgagtctg ttccgctgat gaattttgcc tgctcgacat   720
```

```
cgtttctgcg acatgcgat cgacgagatc tttgcgttag acgccgttgg gaagggactc      780
ggaggtgggt ttagacctgc gtggtagaag aatgggacga gtatatgagt agagtaccgc      840
gtcgataccg cgtaaccgtg catgtgctac tactccttga ccgctgattg gttgcgaact      900
cgacatgatc taggtcgtcc tcgtctggac tcctaatcaa gagagacaag agaatggttg      960
aggagctgct caaattttgg cggataacgt cgtcggtatc ctatgaatct acgttgtgta     1020
tctctaatgc tttgtacgtc tttgacgcgg taagaattta ggacggaatg cagacgaaat     1080
gacagcgatg acgtaacatc cgattatcag cgcgacagta taaaaggcgc agaattttga     1140
catctctcc                                                             1149

<210> SEQ ID NO 6
<211> LENGTH: 791
<212> TYPE: DNA
<213> ORGANISM: Basidiomycetes

<400> SEQUENCE: 6
tccagcattt tgttcgagag agtcaagact cgaggatacc gctagtcgcc tgtggtctgg       60
atcgttcctt ctatgttcgg tgtctggagc atggccttttc tagactcttg gctggtactg      120
gacgaccaat cacgaggtgc ctgtggcgca cattatggct ctccgtgtgc tccagccaat      180
taggttccgg ggaggggtta tgcattagaa acgatctgtt catctgaaag gtggtatcgc      240
gtttgttgtg tggatgacca ccctagatga ggcctggatg atactgcctt aaaattggag      300
gcgcgtccag ggcgcgtcgt tctccgagtc tgttccgctg atgaattttg cctgctcgac      360
atcgtttctg cggacatgcg atcgacgaga tctttgcgtt agacgccgtt gggaagggac      420
tcggaggtgg gtttagacct gcgtggtaga agaatgggac gagtatatga gtagagtacc      480
gcgtcgatac cgcgtaaccg tgcatgtgct actactcctt gaccgctgat tggttgcgaa      540
ctcgacatga tctaggtcgt cctcgtctgg actcctaatc aagagagaca agagaatggt      600
tgaggagctg ctcaaatttt ggcggataac gtcgtcggta tcctatgaat ctacgttgtg      660
tatctctaat gctttgtacg tctttgacgc ggtaagaatt taggacggaa tgcagacgaa      720
atgacagcga tgacgtaaca tccgattatc agcgcgacag tataaaaggc gcagaatttt      780
gacatctctc c                                                           791

<210> SEQ ID NO 7
<211> LENGTH: 626
<212> TYPE: DNA
<213> ORGANISM: Basidiomycetes

<400> SEQUENCE: 7
tgtgctccag ccaattaggt tccggggagg ggttatgcat tagaaacgat ctgttcatct       60
gaaaggtggt atcgcgtttg ttgtgtggat gaccacccta gatgaggcct ggatgatact      120
gccttaaaat tggagcgcgc tccagggcgc gtcgttctcc gagtctgttc cgctgatgaa      180
ttttgcctgc tcgacatcgt ttctgcggac atgcgatcga cgagatcttt gcgttagacg      240
ccgttgggaa gggactcgga ggtgggttta gacctgcgtg gtagaagaat gggacgagta      300
tatgagtaga gtaccgcgtc gataccgcgt aaccgtgcat gtgctactac tccttgaccg      360
ctgattggtt gcgaactcga catgatctag gtcgtcctcg tctggactcc taatcaagag      420
agacaagaga atggttgagg agctgctcaa attttggcgg ataacgtcgt cggtatccta      480
tgaatctacg ttgtgtatct ctaatgcttt gtacgtcttt gacgcggtaa gaatttagga      540
cggaatgcag acgaaatgac agcgatgacg taacatccga ttatcagcgc gacagtataa      600
```

```
aaggcgcaga attttgacat ctctcc                                      626

<210> SEQ ID NO 8
<211> LENGTH: 13
<212> TYPE: DNA
<213> ORGANISM: Artificial
<220> FEATURE:
<223> OTHER INFORMATION: EGFP-F

<400> SEQUENCE: 8
atggtgagca agg                                                     13

<210> SEQ ID NO 9
<211> LENGTH: 19
<212> TYPE: DNA
<213> ORGANISM: Artificial
<220> FEATURE:
<223> OTHER INFORMATION: EGFP-R

<400> SEQUENCE: 9
tacttgtaca gctcgtcca                                               19

<210> SEQ ID NO 10
<211> LENGTH: 21
<212> TYPE: DNA
<213> ORGANISM: Artificial
<220> FEATURE:
<223> OTHER INFORMATION: hph-F

<400> SEQUENCE: 10
atgaaaaagc ctgaactcac c                                            21

<210> SEQ ID NO 11
<211> LENGTH: 21
<212> TYPE: DNA
<213> ORGANISM: Artificial
<220> FEATURE:
<223> OTHER INFORMATION: hph-R

<400> SEQUENCE: 11
acaacttaat aacacattgc g                                            21
```